United States Patent [19]

Bashir-Hashemi

[11] Patent Number: 5,214,221
[45] Date of Patent: May 25, 1993

[54] NITROCUBANES

[75] Inventor: Abdollah Bashir-Hashemi, Bridgewater, N.J.

[73] Assignee: The United States of America as represented by the Secretary of the Army, Washington, D.C.

[21] Appl. No.: 955,220

[22] Filed: Oct. 1, 1992

[51] Int. Cl.$^5$ ............................................. C07C 205/06
[52] U.S. Cl. ..................... 568/944; 568/941; 568/945; 562/497; 562/498; 560/114; 560/116; 204/157.94; 204/158.1; 204/158.11
[58] Field of Search ................. 568/944, 945, 941; 204/157.94, 158.1, 158.11, 157.86, 157.82; 560/114, 116; 562/497, 498

[56] References Cited

U.S. PATENT DOCUMENTS

| | | | |
|---|---|---|---|
| 3,418,368 | 12/1968 | Dunn et al. | 560/116 |
| 3,517,055 | 6/1970 | Loeffler | 560/116 |
| 3,551,576 | 12/1970 | Loeffler | 562/498 |

Primary Examiner—Robert L. Stoll
Assistant Examiner—Valerie Fee
Attorney, Agent, or Firm—Anthony T. Lane; Edward Goldberg; Edward F. Costigan

[57] ABSTRACT

An efficient direct functionalization of nitrocubanes has been achieved by irradiation of a solution in an oxalyl halide to yield halogenated and halocarbonylated derivatives of nitrocubanes.

1 Claim, No Drawings

NITROCUBANES

GOVERNMENTAL INTEREST

The Government has rights in this invention pursuant to Contract No. DAAA21-89-C-0013 awarded by the U.S. Army.

The invention described herein was made under a contract with the Government and may be used and licensed by or for the Government.

FIELD OF USE

This invention describes the direct functionalization of nitrocubanes via irradiation in the presence of an oxalyl halide.

SUMMARY OF THE INVENTION

A solution of 1,4-dinitrocubane (Eaton, P.E.; et al; J. Org. Chem.; 1984, 49, 185; Eaton, P.E.; Wicks, G.E.; J. Org. Chem.; 1988, 53, 5353) in oxalyl chloride was irradiated under a sunlamp for 12 h at room temperature. After removing oxalyl chloride under reduced pressure, the reaction mixture was hydrolyzed nd partioned between ethyl acetate and 5% aqueous NaOH. From the organic phase was isolated 2-chloro-1,4-dinitrocubane, 3, and 2,5-dichloro-1,4-dinitrocubane, 4. After acidification of the alkaline layer with HCl and extraction with ethyl acetate, 2-carboxy-1,4-dinitrocubane, 5, was obtained in 68% yield.

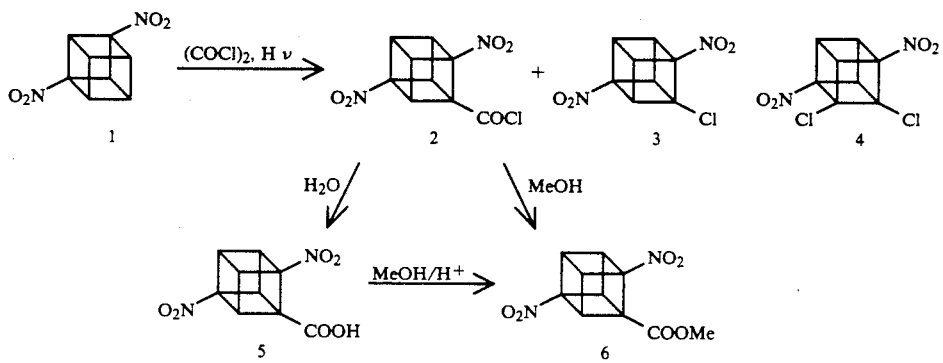

BACKGROUND OF THE INVENTION

Considerable effort in recent years has been directed toward the synthesis of polynitrocubanes because of the potential use of this class of energetic materials as explosives, propellants, fuels and binders (Chemistry of Energetic Materials; Ed., G.A. Olah; D.R. Squire; Academic Press, Inc., San Diego, CA, 1991. also see Carbocyclic Cage Compounds; Ed., E.J. Osawa; O. Yonemitsu; VCH Publishers, Inc., New York, NY, 1992). The compact structures of cage molecules result in high densities, and the introduction of $NO_2$ groups further enhances the density. The strain energy present in the cubane skeleton (>166 kcal/mol) is an added bonus to its performance. Furthermore, preliminary results with polynitrocubanes indicate that such compounds are thermally very stable and are also very insensitive energetic materials. Consequently, it is of interest to introduce functional groups on the cubane skeleton which can be converted to nitro group or other active functionalities.

Direct functionaliztion of nitrocubanes, while an attractive approach, has not heretofore been realized. Cationic or anionic reactions, due to the activity of the nitro groups give either decomposed products or recovered starting materials. We report here an efficient direct functionalization of a nitrocubane molecule by its irradiation in a solution of oxalyl halide (for a related case see Wiberg, K.B.; 10th Annual Working Group Meeting, Jun. 3-6, 1992, Kiamesha Lake, NY. For much simpler cases see Wiberg, K.B; Williams, Jr., V.Z.; J. Org. Chem., 1970, 35, 369; Applequist, D.E.; Saksi, T.; J. Org. Chem.; 1978, 43, 2399). This new and potentially powerful synthetic development will greatly shorten the number of steps necessary to obtain nitrocubane derivatives which are otherwise difficult to synthesize.

The structures of 3,4 and 5 were confirmed by NMR spectrometry. Furthermore, Compound 5 was converted to the corresponding 2-carbomethoxy-1,4-dinitrocubane 6 by esterification using MeOH, and the molecular structure of 6 was confirmed by X-ray crystallographic analysis.

DESCRIPTION OF THE PREFERRED EMBODIMENTS

The following section describes specific experimental procedures used for the synthesis:

A mixture of 1,4-dinitrocubane, 1,(388 mg. 2.0 mmol) in oxalyl chloride (50 mL) was photolyzed under a sunlamp for 18 h at room temperature. Oxalyl chloride was removed on a rotary evaporator and the solid residue was partioned between EtOAc (40 mL) and NaOH solution (5%, 30 mL). After stirring for 3 h, the organic phase was separated, washed with brine, dried over anhydrous $Na_2SO_4$ and concentrated under reduced pressure. The residue was chromatographed on silica gel using hexane/$CH_2Cl_2$(1:1) to give 2-chloro-1,4-dinitrocubane 3, m.p. 145°-147° C.; $^1$H NMR(CDCl$_3$); δ4.84(m, 2H); 4.71 (m, 3H); and 2,5-dichloro-1,4-dinitrocubane, 4, m.p. 188°-190° C.; $^1$H NMR (CDCl$_3$);δ4.90(dd, 2H); 4.78 (dd,2H).

The alkaline layer was acidified with HCl (10%) and organic materials were extracted with EtOAc (2×30 mL). The organic phase was washed with brine, dried over $Na_2SO_4$, and concentrated via rotary evaporator to give 400 mg or a crude product which was triturated with hexane/acetone 10:1, (5.0 mL) to give 2-carboxy-1,4-dinitrocubane, 5, m.p. 187-189 (Dec)° C.; $^1$H NMR (acetone-d$_6$);δ4.96 (m,2H); 4.74 (m, 3H).

Compound 5 (100 mg, 0.4 mmol) was stirred with MeOH (20 mL) and MeSO$_3$H(4 drops) at reflux overnight. The reaction mixture was concentrated and then dissolved in ethyl acetate (20 mL). The solution was washed with aqueous $Na_2CO_3$ (5%), then brine, dried over anhydrous $Na_2SO_4$ and concentrated. The residue was triturated with ether/hexane (1:1) to give 2-carbomethoxy-1,4-dinitrocubane 6 m.p. = 165° C.; $^1H$ NMR ($CDCl_3$), δ4.92 (M,2H); 4.62 (m, 3H), 3.80 (s,3H).

In another experiment the solid residue from the reaction of 1,4-dinitrocubane (100 mg) and oxalyl chloride (20 mL) under a sunlamp (vide supra was treated with methanol (20 mL) for 4 h at room temperature. The excess methanol was evaporated and the residue was dissolved in ethyl acetate (20 mL). The organic layer was washed with 5% aqueous $Na_2CO_3$ and then brine. After drying over $Na_2SO_4$ and then concentration, the crude product was chromatographed on silica gel using hexane;$CH_2Cl_2$ (1:1) to give compounds 3,4, and 6.

What is claimed is:

1. 2-carbomethoxy,-1,4-dinitrocubane.

* * * * *